US012660993B2

(12) United States Patent
Thaha et al.

(10) Patent No.: US 12,660,993 B2
(45) Date of Patent: Jun. 23, 2026

(54) LOCOMOTION SYSTEM FOR A MEDICAL DEVICE

(71) Applicant: Queen Mary University of London, London (GB)

(72) Inventors: Mohamed Adhnan Thaha, London (GB); Mohammad Hasan Shaheed, London (GB); Julius Esmann Bernth, London (GB)

(73) Assignee: Queen Mary University of London, London (GB)

( * ) Notice: Subject to any disclaimer, the term of this patent is extended or adjusted under 35 U.S.C. 154(b) by 457 days.

(21) Appl. No.: 18/043,099

(22) PCT Filed: Sep. 15, 2021

(86) PCT No.: PCT/EP2021/075342
§ 371 (c)(1),
(2) Date: Feb. 27, 2023

(87) PCT Pub. No.: WO2022/058354
PCT Pub. Date: Mar. 24, 2022

(65) Prior Publication Data
US 2024/0023794 A1 Jan. 25, 2024

(30) Foreign Application Priority Data

Sep. 16, 2020 (GB) ..................................... 2014594

(51) Int. Cl.
*A61B 1/04* (2006.01)
*A61B 1/00* (2006.01)
(Continued)

(52) U.S. Cl.
CPC .......... *A61B 1/041* (2013.01); *A61B 1/00156* (2013.01); *A61B 1/045* (2013.01);
(Continued)

(58) Field of Classification Search
CPC ..... A61B 1/041; A61B 1/00156; A61B 1/045; A61B 5/42; A61B 5/6861; H02K 33/18;
(Continued)

(56) References Cited

U.S. PATENT DOCUMENTS

| | | | |
|---|---|---|---|
| 2012/0079915 A1 | 4/2012 | Choi | |
| 2012/0119596 A1* | 5/2012 | Doll | H02K 16/02 |
| | | | 310/36 |

(Continued)

FOREIGN PATENT DOCUMENTS

| | | |
|---|---|---|
| CN | 104027060 | 9/2014 |
| EP | 2792299 | 10/2014 |

(Continued)

OTHER PUBLICATIONS

Zabulis, Xenophon et al., "Effects of Vibratory Actuation on Endoscopic Capsule Vision", 30th Annual International IEEE Embs Conference., Aug. 20-24, 2008. 4 pages.
(Continued)

*Primary Examiner* — Michael Andrews
(74) *Attorney, Agent, or Firm* — DeWitt LLP

(57) ABSTRACT

A locomotion system for use in a medical device, including at least one magnet, a rotor including a plurality of coil windings, and a ferromagnetic member. The rotor is configured, on application of a current to the plurality of coil windings, to travel along the ferromagnetic member and to impact on a surface.

17 Claims, 6 Drawing Sheets

SECTION B-B

(51) Int. Cl.

| | |
|---|---|
| *A61B 1/045* | (2006.01) |
| *A61B 5/00* | (2006.01) |
| *H02K 33/18* | (2006.01) |
| *H02K 21/14* | (2006.01) |

(52) U.S. Cl.

CPC .............. *A61B 5/42* (2013.01); *A61B 5/6861* (2013.01); *H02K 33/18* (2013.01); *A61B 2560/02* (2013.01); *A61B 2560/0406* (2013.01); *A61B 2562/162* (2013.01); *H02K 21/14* (2013.01)

(58) Field of Classification Search

CPC ........ H02K 33/16; H02K 33/12; H02K 33/02; H02K 35/04; H02K 41/0356

USPC ................................... 310/12.16, 15, 17, 20

See application file for complete search history.

(56) References Cited

U.S. PATENT DOCUMENTS

| | | | | |
|---|---|---|---|---|
| 2014/0139052 | A1* | 5/2014 | Kawarai ................ | H02K 35/02 310/28 |
| 2014/0378760 | A1* | 12/2014 | Ito ...................... | A61B 1/00158 604/95.01 |
| 2017/0360283 | A1* | 12/2017 | Kimura .................. | A61B 1/041 |
| 2018/0281020 | A1* | 10/2018 | Katada ................... | B06B 1/045 |
| 2020/0315541 | A1* | 10/2020 | Ben-Tsur ............. | A61B 5/4836 |

FOREIGN PATENT DOCUMENTS

| | | |
|---|---|---|
| JP | 2005133145 | 5/2005 |
| JP | 2006280638 | 10/2006 |
| JP | 2006305695 | 11/2006 |
| JP | 2006305695 A | 11/2006 |
| KR | 1020110052405 | 5/2011 |
| KR | 1020110056438 | 5/2011 |
| KR | 1020110066238 | 6/2011 |
| KR | 1020110066239 | 6/2011 |
| KR | 1020110066983 | 6/2011 |
| WO | WO2004041068 | 5/2004 |
| WO | WO2011121532 | 10/2011 |
| WO | WO2014054807 | 4/2014 |
| WO | WO 2014054807 A1 | 4/2014 |
| WO | WO2019201782 | 10/2019 |

OTHER PUBLICATIONS

Carpi, Federico et al., "Magnetically Controllable Gastrointestinal Steering of Video Capsules", IEEE Transactions on Biomedical Engineering. vol. 58, No. 2., Feb. 2011. 4 pages.

Ciuti, G. et al., "A Wireless Module for Vibratory Motor Control and Inertial Sensing in Capsule Endoscopy", ScienceDirect. Procedia Engineering., (2011). pp. 92-95.

Su, Gang et al., "A Design of the Electromagnetic Driver for the "Internal Force-Static Friction" Capsubot", IEEE/RSJ International Conference on Intelligent Robots and Systems. Oct. 11-15, 2009. pp. 613-617.

Written Opinion for International Application No. PCT/EP2021/0745342 date mailed Dec. 22, 2021.

International Search Report for PCT/EP2021/075342 dated Dec. 22, 2021, 5 pages.

* cited by examiner

SECTION B-B 102          104          108

300

106          112

200

202

100

300

200

202

SECTION A-A

400

500

414

406

412

406

412

SECTION A-A

500

414

LOCOMOTION SYSTEM FOR A MEDICAL DEVICE

RELATED APPLICATIONS

This application claims priority from Application PCT/EP2021/075342, filed Sep. 15, 2021, and claims priority from Great Britain Patent Application No. 2014594.2, filed Sep. 16, 2020, each of which are incorporated by reference in their entireties in this application.

TECHNICAL FIELD

The present disclosure relates to a locomotion system for use in a medical device such as an endoscopic capsule.

BACKGROUND

Miniaturized medical devices, such as endoscopic capsules, offer many significant benefits over traditional methods of diagnosing and treating patients. In particular, most miniaturized medical devices can be easily inserted into the human body with minimal discomfort or risk. Once inside the body, the small size of such devices offers greater versatility for performing diagnosis, drug delivery and other therapies.

To take the example of an endoscopic capsule, such a capsule can be swallowed by a patient in the same manner as an ordinary pill. This removes the need for more involved and invasive procedures associated with traditional endoscopies, where a camera on the end of a cable is inserted into the body. A capsule endoscope typically includes a camera. As the capsule passes through the body, in particular the digestive tract, the camera can take many thousands of images. These images can be processed and can aid in diagnosis of bowel diseases and such like.

Traditionally, a capsule endoscope travels through the digestive tract in the same manner as any other ingested item. That is, the capsule is propelled along the digestive tract by contractions of the respective organs and muscles of the stomach, intestine and so on. This limits the utility of the device, because the speed at which the capsule moves is dependent on the biology of the patient and cannot be effectively controlled by an external operator. The capsule position can also not be effectively controlled or modified, which makes it difficult to focus the procedure on critical sections of the digestive tract.

Some attempts to mitigate these problems have been suggested, such as providing an endoscopic capsule with its own locomotion mechanism, so as to enable the capsule to move of its own accord in response to operator instructions. However, existing systems of this nature have also encountered problems. In particular, generating sufficient force to drive the capsule in a particular desired direction has proved challenging, given the restrictions on the size of the capsule and the need to overcome frictional forces generated by the internal walls of the digestive tract.

It would therefore be advantageous to provide systems and methods which provide for improved locomotion of a medical device, such as a capsule endoscope, when inside the body.

SUMMARY

This summary introduces concepts that are described in more detail in the detailed description. It should not be used to identify essential features of the claimed subject matter, nor to limit the scope of the claimed subject matter.

According to one aspect of the present disclosure, there is provided a locomotion system for use in a medical device, comprising at least one magnet, a rotor comprising a plurality of coil windings and a ferromagnetic member. The rotor is configured, on application of a current to the plurality of coil windings, to travel along the ferromagnetic member and to impact on a surface.

The motion of the rotor along the ferromagnetic member is caused by the electromagnetic interaction between the at least one magnet and the plurality of coil windings when a current is passed through the windings.

The rotor can be considered an actuator and can impart motion to a medical device in which the locomotion system is provided. In further detail, when the locomotion system is incorporated in a medical device, the impact force generated by the rotor striking the surface is transferred to the medical device as a whole. The impact force can thereby propel the medical device in a particular direction. Accordingly, when provided in a capsule endoscope or similar device, the disclosed locomotion system provides a mechanism to control the position of the medical device within the body.

Moving the medical device through use of an impact-based mechanism rather than, for example, an external magnetic mechanism or a system based on inertial movement increases the likelihood that the device is able to overcome frictional forces acting on the device when inside the body. In particular, an impact transfers momentum quickly over a short period of time. This results in a greater overall driving force than an inertial-based mechanism, where acceleration and deceleration occur over a longer time period.

The ferromagnetic member, along which the rotor travels during actuation, acts to guide the magnetic field from the one or more magnets. In particular, the field is guided toward the ferromagnetic member. As a result, the magnetic field density across the plurality of coil windings of the rotor as it travels along the ferromagnetic member is greater, because dissipation of the magnetic field is reduced. Additionally, the channelling effect provided by the ferromagnetic member causes the magnetic field to be arranged more perpendicularly to the coil windings as the rotor travels along the ferromagnetic member. As a result, the acceleration experienced by the rotor is stronger because the direction of the net electromotive force is closer to being parallel with the direction of travel.

Providing a denser and more perpendicular magnetic field results in greater and more uniform acceleration of the rotor. As a result, the rotor will accelerate toward the impact surface faster and can generate a larger impact force on striking the surface. The larger impact force increases the chance that the medical device is able to move in the desired direction. For example, in the case of a capsule endoscope, the increased impact force increases the likelihood that the capsule is able to overcome the frictional forces of the digestive tract. As can be seen, the disclosed system therefore provides a more effective driving mechanism for a medical device such as a capsule endoscope.

The locomotion system can comprise a housing. The at least one magnet, rotor and ferromagnetic member can be provided within the housing, optionally alongside other components. Optionally, the surface which the rotor impacts can be a surface or wall of the housing.

The ferromagnetic member can be located centrally within the housing. For example, the housing can circumferentially surround the ferromagnetic member.

Optionally, the locomotion system can be such that the rotor is not in sliding contact with the housing as it travels along the ferromagnetic member. If the rotor is in sliding contact with the housing as it travels, it experiences a significant frictional force. This can slow the rotor down and reduce the driving force which the rotor is able to provide. Avoiding sliding contact between the housing and the rotor as it moves avoids this issue.

One way to avoid sliding contact between the rotor and the housing can be to have the rotor interface with and/or be in contact with the ferromagnetic member as it travels, instead of the housing. As the ferromagnetic member has a smaller diameter than the housing, it also has a smaller surface area acting to provide friction on the rotor as it moves. The frictional force acting on the rotor is therefore less than if the rotor were in sliding contact with the housing as it moved.

Optionally, the ferromagnetic member can comprise a rod or rail. In that case, the rotor can engage the rod or rail as it moves along. For example, the rotor can be configured to slide along the rod or rail.

The rotor can surround at least a portion of the ferromagnetic member. For example, the ferromagnetic member can run through the rotor. The ferromagnetic member can be attached to and/or support the weight of the rotor, or another element of the locomotion system can perform this function instead or in addition.

Optionally, the rotor can comprise a carriage around which is wound the plurality of coil windings.

The wire diameter of the rotor coil windings can be between 0.03 mm and 0.3 mm inclusive. A "winding" in this context is to be interpreted as a section or loop of wire. The plurality of coil windings can be formed by a single wire or by a plurality of wires.

The locomotion system can comprise a plurality of magnets. The plurality of magnets can be arranged circumferentially around the rotor and ferromagnetic member. The term "circumferentially" is to be interpreted broadly as meaning that the magnets substantially surround the ferromagnetic member and/or rotor, but does not necessarily imply that the magnets form a circle.

The ferromagnetic member can be provided at the centre of the magnets. This can advantageously maximise the channelling effect of the ferromagnetic member on the magnetic field.

Each magnet can be configured such that the same polar face of each magnet (i.e. the "North" or "South" face) faces toward the rotor and ferromagnetic member. If a housing is provided, the plurality of magnets can be provided within the housing between the housing and the rotor and ferromagnetic member.

The locomotion system can comprise a returning element configured to repel the rotor from the impact surface. For example, the returning element can comprise a spring or an additional magnet. The term "spring" is to be interpreted broadly as any resilient and/or elastic component operable to repel the rotor from the impact surface. The returning element can be configured to return the rotor to a starting position after it has struck the surface. Alternatively or additionally, this returning action can be achieved by changing the polarity of the current flowing through the coil windings of the rotor.

According to another aspect of the present disclosure, there is provided a locomotion system for use in a medical device, comprising a ferromagnetic enclosure, a plurality of coil windings, and a rotor comprising at least one magnet. The rotor is configured, on application of a current to the plurality of coil windings, to travel along the ferromagnetic enclosure and to impact on a surface.

According to a further aspect of the present disclosure, there is provided an endoscopic capsule comprising a locomotion system as disclosed herein. Such an endoscopic capsule can be able to traverse the intestinal tract more effectively due to the increased force provided by the actuation mechanism of the locomotion system.

According to a yet further aspect of the present disclosure, there is provided a method of moving a medical device comprising a locomotion system as disclosed herein. The method comprises applying a first current to the plurality of coil windings to cause the rotor to travel along the ferromagnetic member or ferromagnetic enclosure in a first direction and impact on a surface. The rotor impacting on the surface generates motion of the medical device in the first direction.

By repeatedly causing the rotor to impact on the surface in this manner, the impact force can be transferred to the medical device. The medical device can thereby be driven through the body, for example the digestive tract, in a desired direction. This provides greater control over the medical procedure being performed. In particular, a medical practitioner can be able to more easily target specific sections of the body for imaging, drug delivery or some other therapeutic intervention.

Optionally, the method comprises moving the rotor in a second direction away from the impact surface. This can be considered as resetting the rotor or actuation mechanism. The rotor can be moved in the second direction back to a start position, before being moved in the first direction to strike the surface once again.

Moving the rotor in the second direction can comprise applying a second current to the plurality of coil windings. Said second current can have an opposite polarity to the first current such that application of the second current causes the rotor to travel along the ferromagnetic member in the second direction. The second current can be of a lower magnitude than the first current and/or can be applied for a shorter duration than the first current. This can ensure that the impact force generated by the rotor in the first direction is greater than any impact or inertial forces generated by the rotor in the second direction. Alternatively, a returning element such as a spring or an additional magnet can be used to move the rotor in the second direction, as described above.

According to a yet further aspect there is provided a method for the diagnosis of a disease or condition in a patient using a medical device comprising of a locomotion system as disclosed herein, comprising the steps of generating images of the gastrointestinal tract and analysing said images to provide a diagnostic indicator of whether the patient has a disease or condition.

For example, the disease or condition can be cancer. The disease or condition can be polyp in the large or small intestine, stomach or oesophagus. The disease or condition can be a gastrointestinal disease, for example a gastrointestinal disease characterised by inflammation, for example Crohn's Disease, Ulcerative colitis, Indeterminate colitis or Irritable Bowel Syndrome (IBS).

The method can further comprise guiding the device to a pre-determined location of the gastrointestinal tract. The device can be guided by wireless communication with a remote control activating and deactivating the locomotion device within the device.

The disease or condition can be a gastrointestinal disorder, inflammation, injury or cancer. The gastrointestinal disorder can be oral disease, oesophageal disease, gastric disease, intestinal disease or accessory digestive gland disease. Examples of gastrointestinal disorders include constipation, irritable bowel syndrome, haemorrhoids, anal fissures, perianal abscesses, anal fistulas, diarrhoea, perianal infections, diverticular diseases, colitis, colon polyps, Crohn's disease, Celiac disease, gall stones, bile duct stones, bile duct strictures, gastroesophageal reflux disease (GERD) or peptic ulcer disease (PUD).

BRIEF DESCRIPTION OF THE DRAWINGS

Illustrative implementations of the present disclosure will now be described, by way of example only, with reference to the drawings. In the drawings.

Throughout the description and the drawings, like reference numerals refer to like features.

DETAILED DESCRIPTION

Figure 1A:
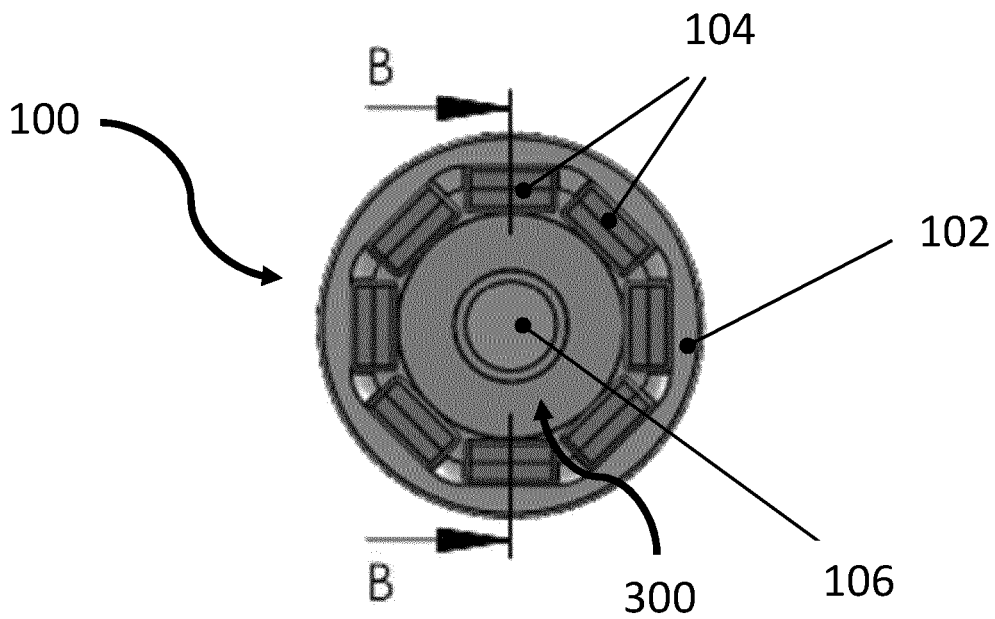
FIGS. 1*a* and 1*b* depict an example first embodiment of the locomotion system of the present disclosure.
Figure 1B:
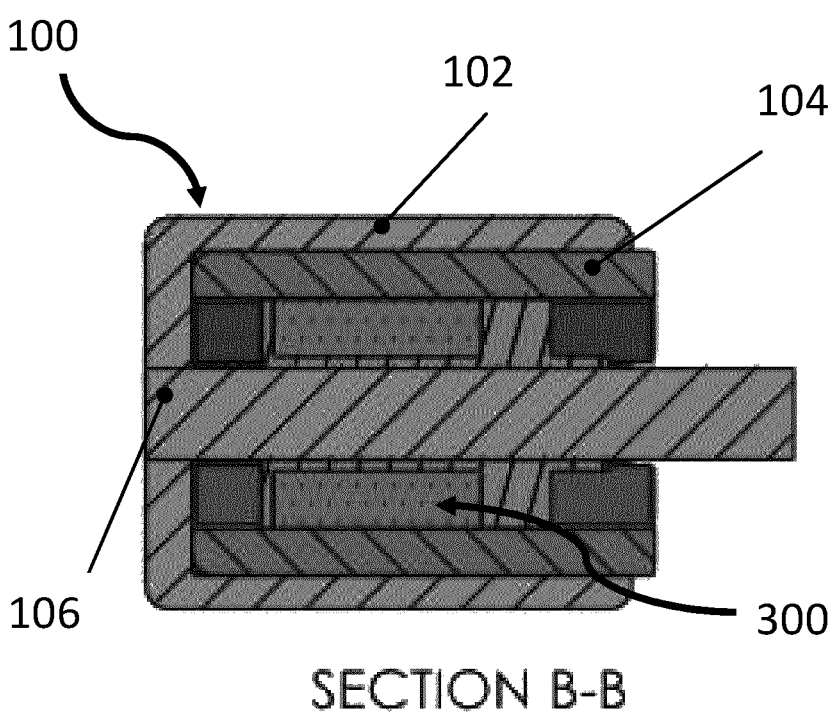
Figure 2:
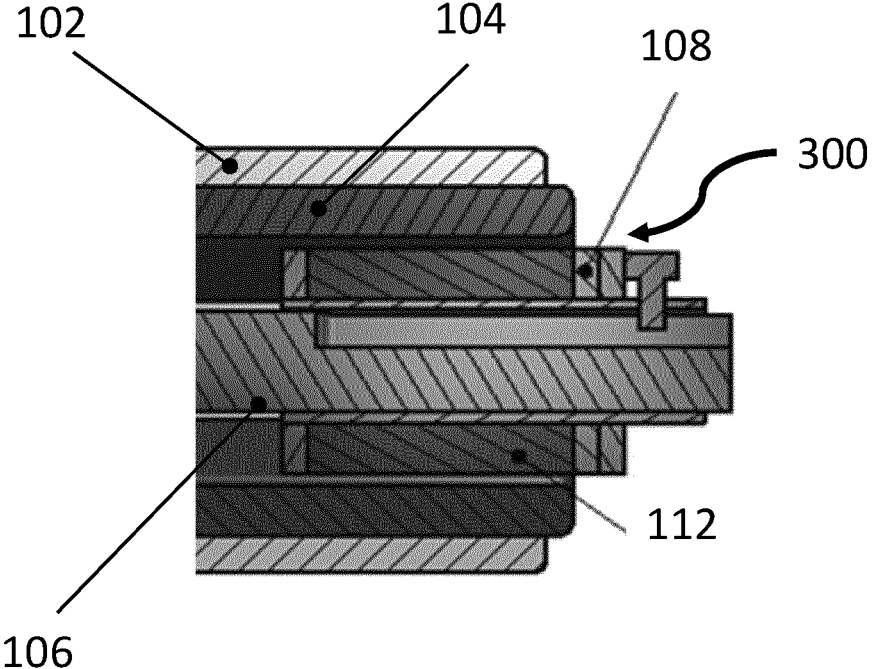
FIG. 2 depicts a rotor of the first example embodiment in greater detail.

This detailed description describes, with reference to FIGS. 1*a*, 1*b*, and 2 an example locomotion system according to a first embodiment of the present disclosure. Incorporation of the locomotion system in an example medical device is then described with reference to FIGS. 3*a* and 3*b*. An alternative embodiment of the locomotion system is described with reference to FIGS. 4*a* and 4*b*. Finally, example operation of the locomotion system is described with reference to FIGS. 5, 6*a* and 6*b*.

The systems disclosed herein relate generally to a locomotion system for use in a medical device, in particular a miniaturized medical device such as an endoscopic capsule. The term "miniaturized medical device" in this context is intended to mean a device which can be wholly inserted into the body and which typically travels around or through the body by virtue of its own propulsion or drive system, or as a result of the body naturally passing the device through a particular biological structure such as the digestive tract. This is in contrast to traditional larger scale medical devices such as cable-based endoscopes, which remain physically connected to the outside world during operation.

A locomotion system for a medical device according to a first embodiment comprises at least one magnet and a rotor comprising a plurality of coil windings. When a current is provided to the plurality of coil windings, the resultant magnetic field generated around the coil windings interacts with the magnetic field(s) of the magnet(s). The resultant force causes the rotor to travel in a certain direction along a ferromagnetic member, until the rotor impacts an impact surface. The resulting impact force is able to generate motion of the medical device.

An example arrangement of such a locomotion system will now be described in greater detail with respect to FIGS. 1*a* and 1*b*.

FIG. 1*a* depicts an end-on, cross-sectional view of an example locomotion system 100 of the first embodiment of the present disclosure. The locomotion system 100 comprises a housing 102, which in this example is made of maraging steel. In this example the housing 102 is cylindrical on its outside and thus has a circular outer cross-section. In this example the housing 102 has an octagonal inner shape, and thus has an octagonal inner cross-section. The housing can alternatively take a different shape and have a different inner and outer cross-section.

The locomotion system 100 further comprises a plurality of magnets 104. In this embodiment there are eight magnets, with one magnet arranged on each of the eight inner faces of the housing 102. The North face of each magnet faces inwards into the centre of the locomotion system 100 in this example. The magnets 104 thus form a circumferential ring around the centre of the locomotion system 100. The terms "circumferential" and "ring" are in this context to be interpreted broadly, and are not limited to a precise circular arrangement. In other examples, the magnetic field could be provided by a single or a plurality of tube shaped magnets.

At the centre of the locomotion system 100 is provided a ferromagnetic member 106. In this embodiment, the ferromagnetic member 106 is cylindrical and runs along the central length of the housing 102, as is more apparent from FIG. 1B. In this example the ferromagnetic member 106 is made of steel and is press-fitted into a slot at the back of the housing 102 to firmly secure it to the housing 102. In this example the ferromagnetic member 106 is made from steel such as mild steel.

The locomotion system 100 also comprises a rotor 300. In this example of the first embodiment the rotor 300 comprises a sled or carriage 108 and a plurality of windings 112 wound around the carriage 108, as will be discussed in relation to FIG. 2.

In this example the rotor 300 is slotted over the central ferromagnetic member 106. The fit is such that the rotor 300 is freely able to slide along the ferromagnetic member 106. The ferromagnetic member 106 can in this example therefore be considered a rail, track or guide.

In other examples there can be no direct contact between the ferromagnetic member 106 and the rotor 300. For example, the rotor 300 can be attached to and supported by another component of the locomotion system 100 such as the housing 102, such that there is an air gap between the rotor 300 and ferromagnetic member 106 as the rotor 300 moves along the member 106.

Turning now to FIG. 1B, the example locomotion system 100 of FIG. 1*a* is shown in side cross-section, from view B-B indicated in FIG. 1*a*.

As can be seen, the ferromagnetic member 106 passes through and beyond the full length of the housing 102 in this example and is press fitted into the housing 102 at one end, to the left side of FIG. 1B. The housing 102 defines a volume in which the rotor 300 can travel freely along the ferromagnetic member 106. In this example the magnets 104 extend along almost the entire length of this volume.

The structure of the rotor 300 in this example of the first embodiment can be more clearly discerned from FIG. 2. As can be seen, the rotor 300 comprises a plurality of coil windings 112 provided around a carriage 108. In this example the coil windings 112 are wound around the carriage 108 such that they form a cylindrical winding volume or armature around the ferromagnetic member 106. In this example the rotor sled 108 is made from a non-magnetic material.

In this example the windings 112 are formed from enamel coated copper wire or "magnet wire". In this example, a very thin wire gauge is used to ensure that a very high number of windings 112 around the carriage 302 can be provided. This improves the function of the device by increasing the density of the magnetic field produced when current is passed through the coil windings 112. In this example, a wire outer diameter of 0.2 mm is used. Depending on the available voltage, the wire gauge can be altered to match the resistance to the available current.

The locomotion system of the present disclosure can be provided inside or as part of a medical device, to enable the medical device to move inside the human body in a desired direction and/or at a desired speed. This can provide an operator with increased control over the position of the medical device during a medical procedure. The medical device can comprise multiple components, for example multiple endoscopic capsules.

Figure 3A:
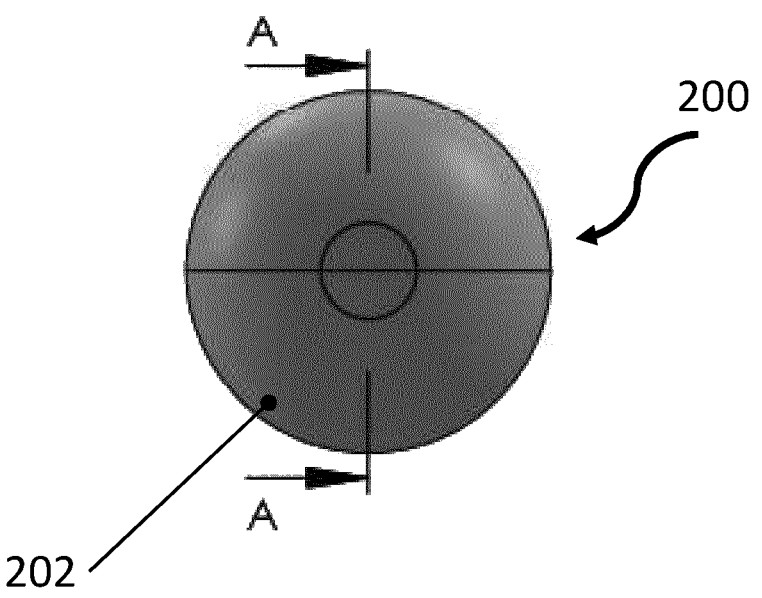
FIGS. 3*a* and 3*b* depict an example medical device in which the locomotion system can be incorporated.
Figure 3B:
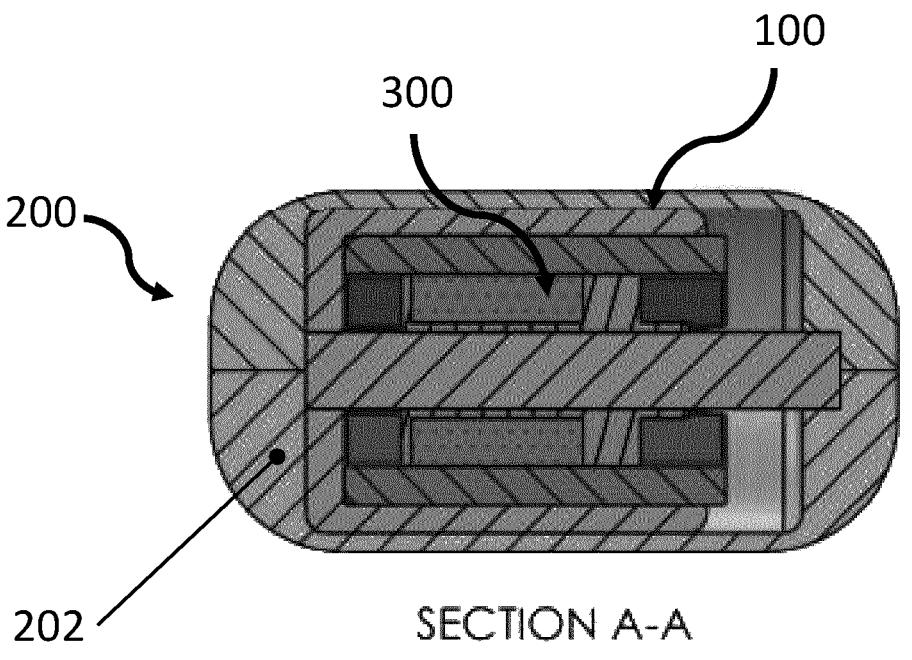

An example medical device in which the locomotion system of the present disclosure can be provided is a capsule endoscope. A capsule endoscope 200 comprising the example locomotion system 100 of FIGS. 1*a* and 1*b* is shown in FIGS. 3*a* and 3*b*. FIG. 3*a* depicts the capsule end-on. FIG. 3*b* depicts the capsule in side-on cross-section, from view A-A shown in FIG. 3*a*.

The capsule endoscope 200 comprises a capsule shell or casing 202. The locomotion system 100 is provided fully inside the casing 202 in this example. The capsule endoscope 200 can also comprise components to enable the capsule to conduct imaging. These are not shown in FIGS. 3*a* and 3*b* for simplicity.

It will be appreciated that the size and shape of the capsule endoscope 200 is entirely optional and can change depending on which imaging are included in the capsule alongside the locomotion system 100. The capsule endoscope 200 can also comprise its own power source, or it can be powered by an external source. The capsule endoscope 200 can comprise a control module configured to receive a control signal from an external controller and direct movement of the capsule accordingly. Such power and control-related components of the capsule are again not shown in FIGS. 3*a* and 3*b*, for simplicity.

A second embodiment of the disclosed locomotion system will now be described with reference to FIGS. 4*a* and 4*b*. The system is shown in head-on cross section in FIG. 4*a*, and in side-on cross section in FIG. 4*b* (from view A-A, indicated in FIG. 6*a*). The second embodiment system can be incorporated into a medical device in the same way as the first embodiment, and so the above discussion in relation to FIGS. 3*a* and 3*b* applies similarly to the second embodiment.

According to this second embodiment, a locomotion system 400 for a medical device is provided and comprises a ferromagnetic enclosure 406. A plurality of coil windings 412 are provided and, in this example of the second embodiment, are wound around the ferromagnetic enclosure 406. The detail of the coil windings is not shown in FIGS. 4*a* and 4*b* for simplicity.

As in the first embodiment, the locomotion system 400 of the second embodiment comprises a rotor 500. However, in contrast to the first embodiment, the rotor 500 of the second embodiment comprises a magnet.

The system of the second embodiment is configured such that, on application of a current to the plurality of coil windings 412, the magnet 500 travels along the ferromagnetic enclosure 406 to impact on a surface. As seen in FIG. 4*b*, the magnet 500 thus moves from left to right (and/or right to left) on application of a current to the windings 412, in the same manner that the rotor 300 of the first embodiment moved.

Accordingly, as will be appreciated, the second embodiment is very similar to the first embodiment except that in the second embodiment the plurality of coil windings remain stationary and the magnet moves. This is in contrast to the first embodiment which has this the other way around. Put another way, the components acting as the stator and the rotor are swapped in the second embodiment compared to the first embodiment.

In addition, whereas the first embodiment includes a ferromagnetic member 106 along which the rotor 300 travels, the second embodiment comprises a ferromagnetic enclosure 406. The rotor (magnet) 500 of the second embodiment travels along inside the enclosure 406 in the second embodiment. The ferromagnetic enclosure 406 therefore provides the same channelling functionality as the ferromagnetic member 106 did in the first embodiment, by guiding the magnetic field acting between the magnet 500 and the coils 412. Similar benefits are therefore obtained as were described above in relation to the first embodiment. In particular, the ferromagnetic enclosure 406 strengthens the electromagnetic coupling between the plurality of coils 412 and the magnet 500, thereby enabling the system to generate a greater actuation force as described above.

In this example of the second embodiment, the system 400 further comprises a sliding sleeve 414. The magnet 500 is in sliding contact with the sliding sleeve 414 as it travels along the ferromagnetic enclosure. The sliding sleeve 414 for example comprises a low-friction material, optionally polytetrafluoroethylene, PTFE, commonly known as Teflon™. As a result, the sliding sleeve 414 provides a low friction contact guide for the magnet 500. This reduces the heat generated by friction as the magnet 500 moves. This is advantageous because excess friction can demagnetise the magnet 500. Thus, the sliding sleeve 414 provides a mechanism to extend the life of the device and improve reliability.

As in the case of the first embodiment, the locomotion system 400 of the second embodiment can be provided within any suitable medical device, for example an endoscopic capsule. The impact surface can be a surface of the ferromagnetic enclosure 406, a surface of the medical device or a surface of some other housing in which the locomotion system 400 is provided, optionally within the medical device.

Figure 4A:
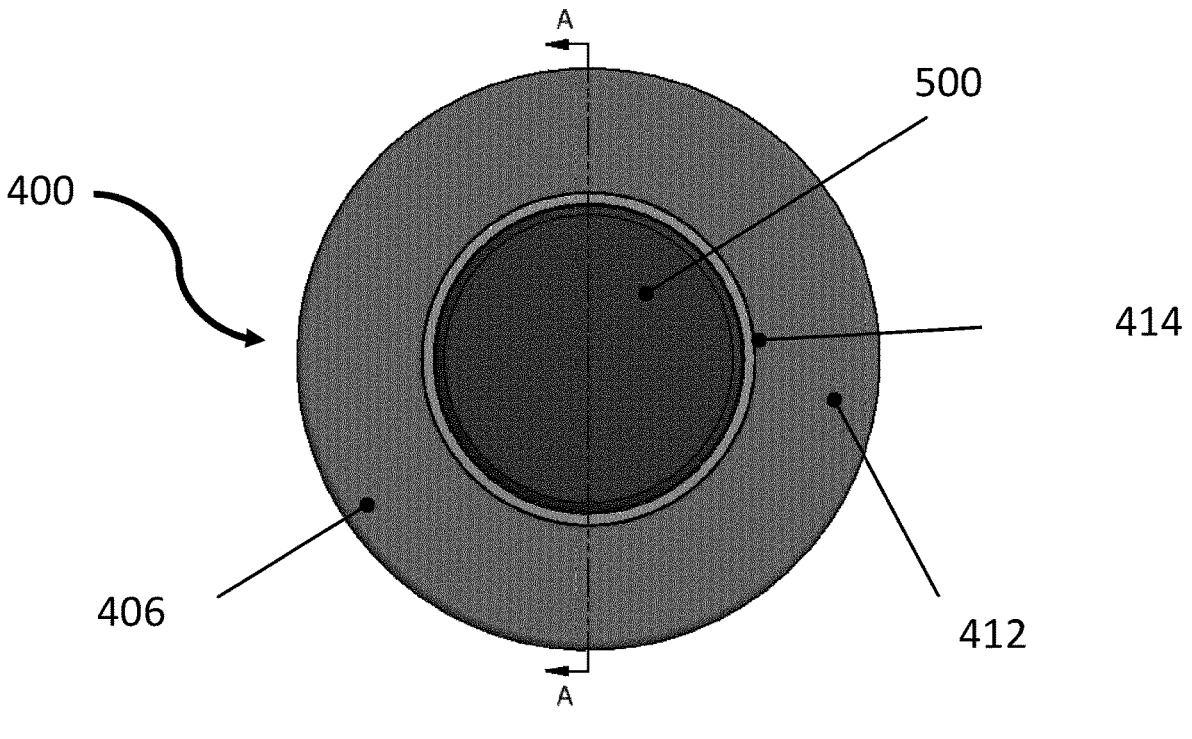
FIGS. 4*a* and 4*b* depict an example second embodiment of the locomotion system of the present disclosure.
Figure 4B:
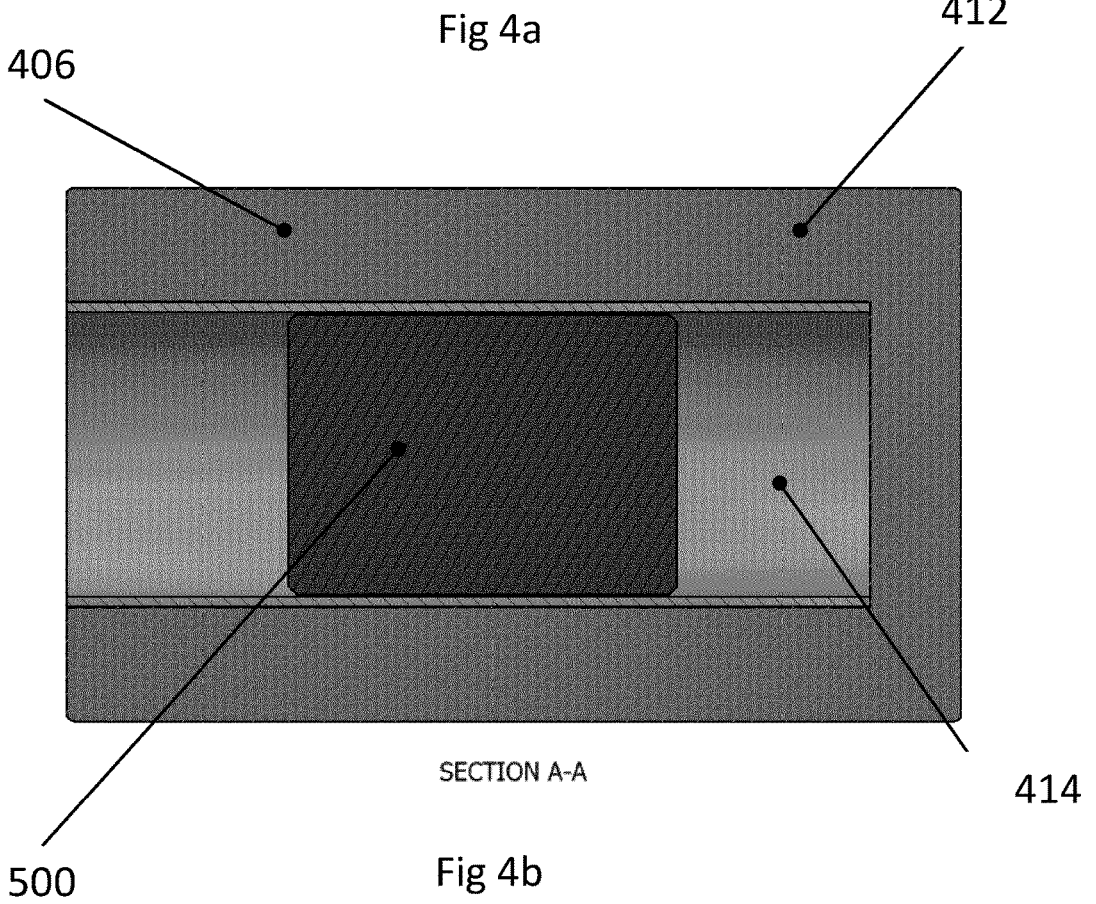

One or more of the ferromagnetic enclosure 406, magnet 500, sliding sleeve 414 and the medical device can have a cylindrical profile, as shown in FIGS. 4*a* and 4*b*. Such an arrangement can improve channelling of the magnetic field.

It will be appreciated that the term "enclosure" is to be interpreted broadly and does not necessitate that the magnet 500 is enclosed on all sides, although this arrangement is also possible. In an example, the enclosure 406 is a tube with one or two open ends, at which are provided impact surfaces. As noted above, the impact surfaces can be surfaces of a housing or surfaces of the medical device in which the locomotion system is provided.

The mechanism to achieve locomotion is the same for both the first and second embodiments of the disclosed locomotion system. At a high level, operation of the locomotion system of either embodiment involves accelerating the rotor 300, 500 by applying a current to the coil windings 112, 412. The rotor 300, 500 is thereby accelerated into an impact a surface, and through this action motion can be generated. This will now be described in further detail with reference to FIGS. 5, 6a and 6b.

Figure 5:
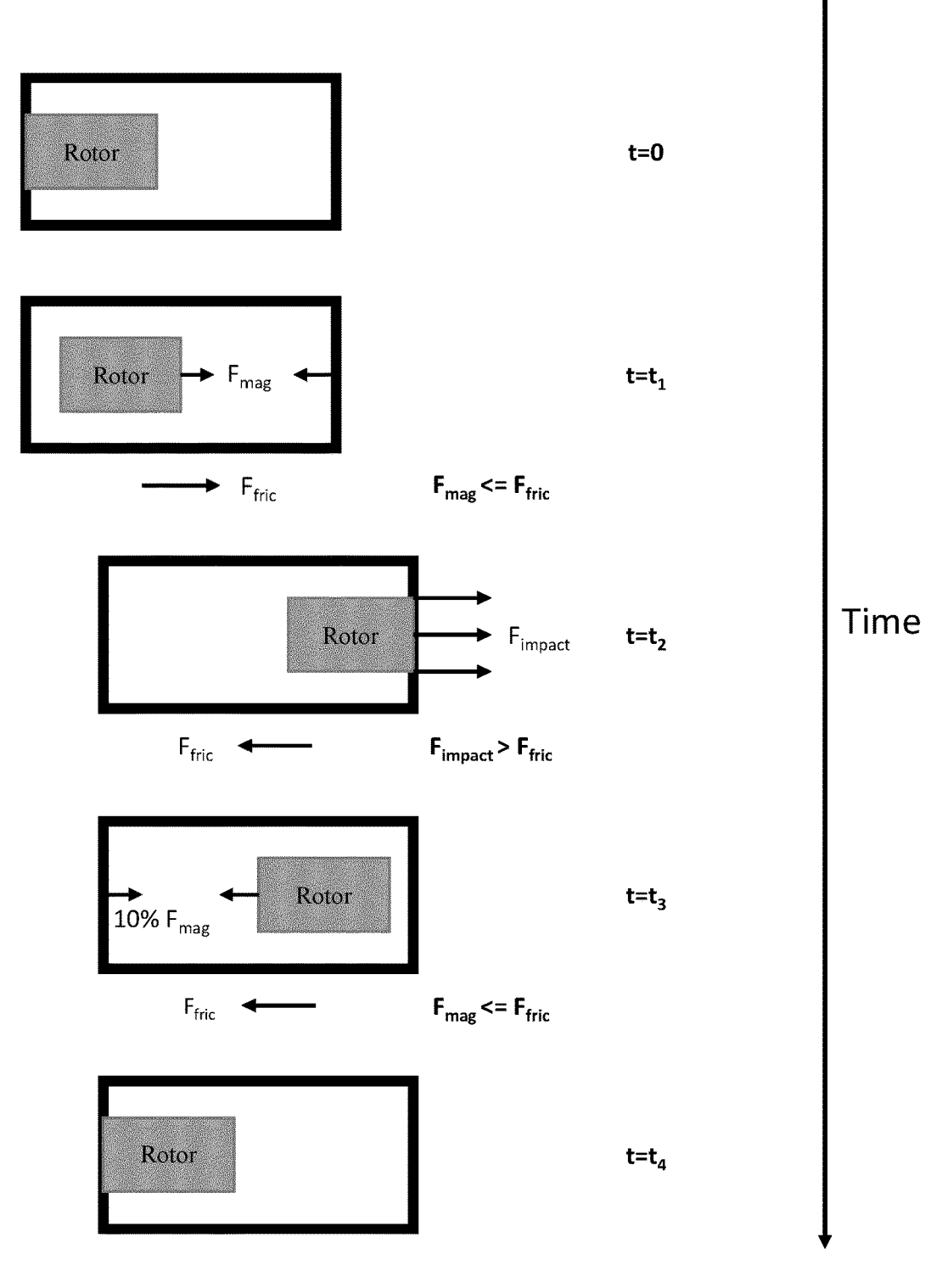
FIG. 5 schematically depicts the operation of the locomotion system and how this system can be used to propel a medical device in a desired direction.

FIG. 5 schematically depicts how the locomotion system of either embodiment of the present disclosure can generate motion of a medical device in a particular direction. The figure depicts a medical device at five different time intervals and demonstrates how the device can move in space as time progresses. For simplicity, FIG. 5 is highly simplified and depicts only the rotor 300, 500 inside the medical device. It is to be appreciated that the other components of the locomotion systems 100, 400 described above in relation to the first and second embodiments respectively, are also present, however these have not been shown for simplicity.

FIG. 5 also depicts the rotor 300, 500 striking a wall of the medical device directly. This is again merely for simplicity. The rotor 300, 500 can strike a wall of the medical device, a wall of the locomotion system housing 102 or any other suitable surface to impart a driving force on the device.

The rotor 300, 500 starting position at time t=0 is shown in the top image of FIG. 5. In this example the rotor 300, 500 starts to the left hand side of the device. To achieve locomotion, a current is passed through the coil windings 112, 412. This generates a magnetic field and said magnetic field interacts with the magnetic field already present by virtue of the surrounding magnets 104 in the first embodiment or the magnet rotor 500 in the second embodiment as described above.

As described by Faraday's Law of Induction, this electromagnetic interaction results in the coils 112 (and therefore the rotor 300, 500) experiencing a force. The direction of this force will be in either direction along the axis of the rotor 300, 500 and ferromagnetic member 106 or enclosure 406 (which in FIG. 5 means either to the left or to the right), depending on the direction (polarity) of the current flowing through the coil windings 112, 412.

The force experienced by the rotor 300, 500 accelerates the rotor 300, 500 in the respective direction, such that the rotor 300, 500 slides along the ferromagnetic member 106 or ferromagnetic enclosure 406. In the present example, the force accelerates the rotor 300, 500 to the right, as shown in FIG. 5, such that at a later time of t=$t_1$ the rotor 300, 500 has moved to the right.

As the rotor 300, 500 is accelerated, the force acting to push the coil to the right ($F_{mag}$) is also acting on the device, but in the opposite direction (i.e. to the left in FIG. 5) due to Newton's third law. In this example, since the device is assumed to be inside a bodily structure such as the intestine, it is assumed that a frictional force acts on the device ($F_{fric}$), and that this will counteract movement of the device. It is assumed that this frictional force is greater than or equal to the force acting on the rotor 300, 500 and device respectively. In mathematical terms, it is assumed that $F_{mag} \leq F_{fric}$. As a result, the device remains stationary during the acceleration of the rotor 300, 500. This is depicted in FIG. 5, where it can be seen that, while the rotor 300, 500 has moved, the device as a whole has not moved between t=0 and t=$t_1$.

Eventually, the rotor 300, 500 impacts an impact surface. As described above, the impact surface could be a surface of the locomotion system housing 102, described above with reference to FIGS. 1a and 1b. Alternatively, the impact surface could be a surface of the medical device, such as a surface of casing 202 of the endoscope 200 described above in relation to FIGS. 3a and 3b.

Regardless of which particular surface is struck by the rotor 300, 500, this action results in the momentum of the rotor 300, 500 being transferred to the surface and thus the device as a whole. This imparts a rapid rightward force on the device. Unlike the initial inertial force, this impact force is large enough to overcome the frictional force acting on the device, because it is provided over a much smaller time-frame (Newton's second law). As a result, the frictional force is overcome and the device jerks forward in the direction that the rotor 300, 500 was moving, i.e. to the right in FIG. 5. This is shown in the third image of FIG. 5, where at t=$t_2$ the force generated by the rotor 300, 500 hitting a surface of the device ($F_{impact}$) has overcome the frictional force ($F_{fric}$) and caused the device as a whole to move to the right. In mathematical terms, $F_{impact} > F_{fric}$.

In order to enable this process to happen repeatedly, the rotor 300, 500 needs to be moved back in the opposite direction (i.e. to the left in FIG. 5) after impact. In the present example, this is achieved by applying a second current to the coil windings 112, 412 of the rotor 300, 500, where the second current is in the opposite direction (opposite polarity) to the original current supplied. This results in a force on the rotor 300, 500 in the opposite direction, so that the rotor 300, 500 moves to the left as shown in the fourth image of FIG. 5, at t=$t_3$.

As in the first instance, it is assumed that the frictional force on the device is sufficient to keep the device in place while the rotor 300, 500 is retracted. This can also be doubly ensured by providing a smaller current when retracting the rotor 300, 500 than when accelerating the rotor 300, 500 into the impact surface. For example, in the example of FIG. 5 the current used to retract the rotor 300, 500 is only 10% of that used to accelerate the rotor 300, 500 into the impact surface, resulting in a force that is only 10% as large. Providing a small current in this manner when retracting the rotor 300, 500 can also ensure that the device remains substantially stationary even if the rotor 300, 500 impacts the back (i.e. left hand in FIG. 5) wall at the end of retraction. This prevents any unwanted back and forth rocking of the device.

Once the rotor 300, 500 has been fully retracted, as shown in the fifth image of FIG. 5 at t=$t_4$, the process can begin again. By repeating this process and selecting an appropriate current value when accelerating and retracting the rotor 300, 500, it will be appreciated that the device can be moved in a desired direction and at a desired speed.

It will be apparent that the process could be reversed. For example, if an impact surface were to alternatively or additionally be provided on the left hand side of the device as shown in FIG. 5, then the rotor 300, 500 could be accelerated to the left to cause leftward motion of the device. Any combination of leftward and rightward motion could then be used to position the device in the desired manner. It will also be appreciated that the terms "left" and "right" have been used herein merely to illustrate the function of the device, and are in no way intended to be limiting. The rotor 300, 500 can move in any desired longitudinal direction inside the device and thereby propel the device along any desired course.

The ferromagnetic member 106 (in the first embodiment) and the ferromagnetic enclosure 406 (in the second embodiment) play an important role in the above-described operation of the device. In particular, the ferromagnetic member 106/enclosure 406 ensure adequate acceleration of the rotor 300, 500, by increasing the flux through the coils 112, 412 of the system as the rotor 300, 500 is accelerated. Without the ferromagnetic member 106/enclosure 406, the magnetic field generated by the magnets 104 or rotor 500 would quickly dissipate as a function of distance from the magnets 104/rotor 500. The direction of the field would also rapidly change as a function of the distance from the magnets 104/rotor 500, causing the rotor 300, 500 to experience a lower net force and thus a lower acceleration.

In the first embodiment, the ferromagnetic member 106 acts to counteract these undesirable effects, by guiding the magnetic field from the magnets 104 to the volume through which the rotor 300 travels. This not only increases the overall strength of the field felt by the rotor 300, but also ensures that the field is more perpendicular to the desired direction of rotor 300 travel. This avoids the field changing direction as it moves away from the magnet surface, ensuring that the net force experienced by the energised coil is maximised.

In the second embodiment, the ferromagnetic enclosure 406 performs a similar function, by guiding the magnetic field from rotor (magnet) 500 to the ferromagnetic enclosure 406 around which are provided coil windings 412. As in the first embodiment, this increases the overall strength of the field felt by the rotor 500 and ensures that the field is more perpendicular to the desired direction of rotor 500 travel. This avoids the field changing direction as it moves away from the magnet surface, ensuring that the net force experienced by the rotor 500 is maximised.

Tests conducted by the inventors indicate the importance of the inclusion of a ferromagnetic element such as ferromagnetic member 106 or ferromagnetic enclosure 406. A comparison was made between a capsule containing the locomotion system 100 described above in reference to FIGS. 1a and 1b, and a similar capsule where the only difference was that no ferromagnetic member was present. That is, the rotor of the comparison device travelled along a member made of non-ferromagnetic material, namely brass. On testing, it was found that use of a ferromagnetic member resulted in a ten-fold increase in the distance moved by the device as a result of a single actuation.

Tests showed that a locomotion system of the type described above in relation to the first embodiment provided in an endoscope capsule enabled the capsule to move with a mean speed of 1.78 cm/s using a supply voltage of 4V. This is sufficient to enable therapeutically useful movement of the capsule endoscope inside the body during a medical procedure. Similar efficacy of a capsule comprising the locomotion system of the second embodiment can be achieved, given the common principles applied in both embodiments.

Figure 6A:
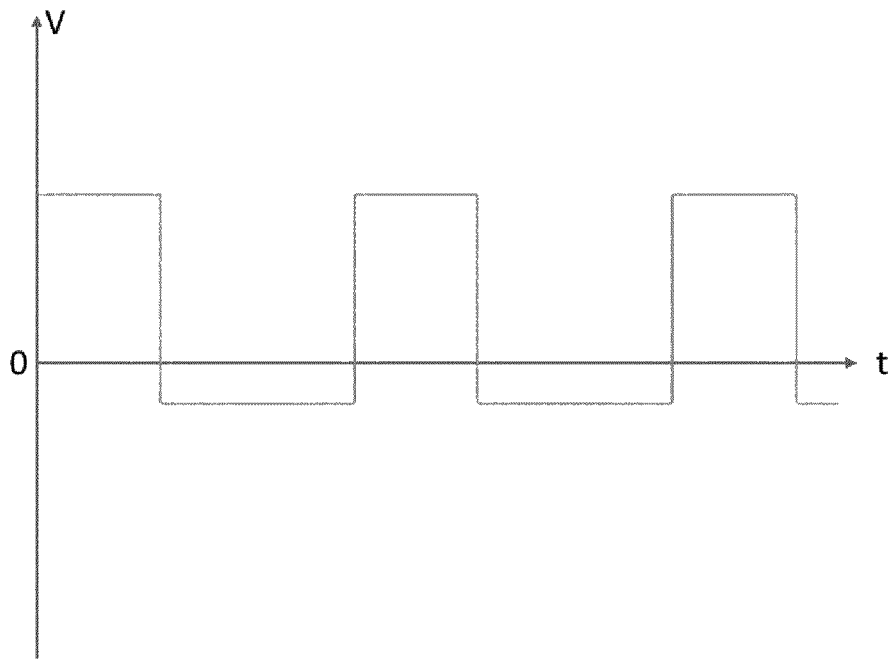
FIGS. 6*a* and 6*b* depict two example voltage waveforms which can be provided to the coils of the rotor to cause it to accelerate.
Figure 6B:
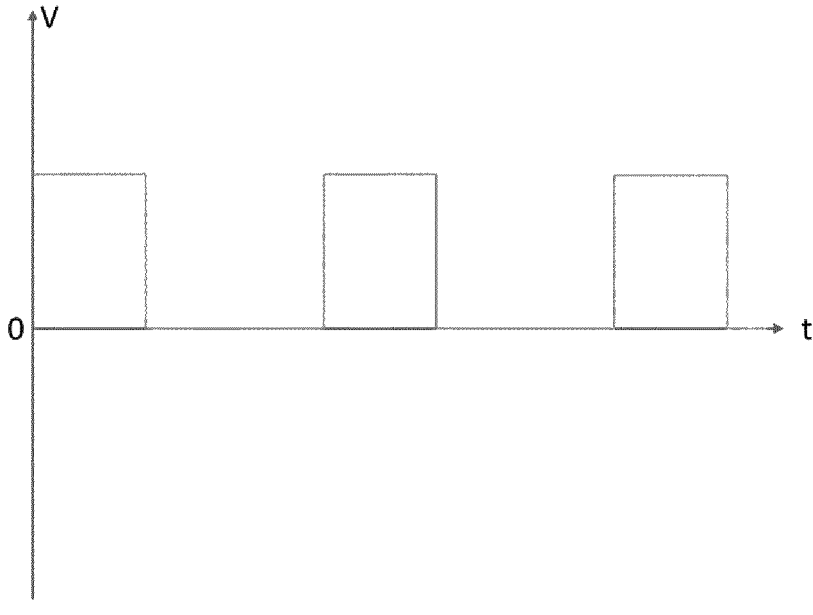

Turning now to FIG. 6a, this FIG. 6a depicts an example voltage waveform that can be provided to the coil windings 112, 412 to achieve the above-described rotor motion.

A first positive pulse is provided to accelerate the rotor 300, 500 towards the impact surface. This is the pulse provided between t=0 and t=$t_2$ of FIG. 5. Once the rotor 300, 500 strikes the impact surface, a second negative pulse of smaller magnitude is provided to retract the rotor 300, 500. This is the pulse provided between t=$t_2$ and t=$t_4$ of FIG. 5.

Once the rotor 300, 500 is fully retracted, another positive pulse is provided to again accelerate the rotor 300, 500 to strike the impact surface, as described above. This process is repeated as many times as desired until the device has been moved to the desired location.

In an alternative arrangement, only positive pulses can be provided and the rotor 300, 500 can be returned to its starting position by other means. For example, the system can comprise a returning element configured to repel the rotor 300, 500 from the impact surface. Examples of returning elements include springs or spring-like elastic components and magnets configured to repel the rotor 300, 500.

Where a returning element is provided, there can be no need for a negative reverse current to be provided to the rotor 300, 500. In this case, only positive pulses need to be provided and so a waveform of the type shown in FIG. 6b can be used.

The above detailed description describes a variety of example arrangements of and methods of using a locomotion system for a medical device. However, the described arrangements and methods are merely examples, and it will be appreciated by a person skilled in the art that various modifications can be made without departing from the scope of the appended claims. Some of these modifications will now be briefly described, however this list of modifications is not to be considered as exhaustive, and other modifications will be apparent to a person skilled in the art.

As described above, the locomotion system can comprise a housing and the rotor can be configured to strike the housing to impart motion to the device. However, this is optional and the rotor can strike any suitable surface of the locomotion system or medical device. In other words, the rotor can transfer momentum directly or indirectly to the medical device as a whole. The locomotion system housing described above is optional.

The arrangement of the magnet(s) of the locomotion system is also entirely optional. All that is required is that the magnet(s) are positioned such that they impart a repelling force on the rotor coils when a current is passed through the coils. The precise number, shape, size, orientation or position of the magnets can be altered depending on the desired functionality and design limitations.

The ferromagnetic member of the first embodiment can be provided in any suitable location within the system. A central location, with the magnets provided circumferentially around, is typically advantageous as this results in the most optimum channelling effect on the magnetic flux. However, this position is not essential and other positions can also provide a suitable channelling effect.

The rotor of the first embodiment may or may not be in sliding contact with the housing or the magnets as it travels along the ferromagnetic member. It is generally advantageous that the rotor is not in sliding contact with the housing or magnets as it moves, so as to avoid frictional forces from these components acting to slow the rotor down. However, in some arrangements some contact between the rotor and the magnets and/or housing can occur.

In the above description of the first embodiment, the rotor slides along the ferromagnetic member. This is optional, and there can be no direct contact between the rotor and ferromagnetic member. In the described arrangements of the first embodiment, the rotor also surrounds the ferromagnetic member. This is advantageous and results in the rotor benefitting maximally from the flux channelling effect of the ferromagnetic member. However, this arrangement is also optional and the rotor can not surround the ferromagnetic member in some arrangements. For example, the rotor can sit on or be provided above/below the ferromagnetic member.

In the described arrangement of the first embodiment, the ferromagnetic member, rotor coils, and magnets are provided circumferentially around one another in concentric rings. This is advantageous because it improves the channelling effect which the ferromagnetic member has on the magnetic flux through the rotor coils. However, this arrangement is optional and alternate arrangements can be used.

The example materials described in relation to components of the above embodiments are in all cases optional.

Motion of the rotor in both embodiments can be controlled by any suitable remote means, for example by a controller sending a Bluetooth signal to a corresponding control module provided in the medical device.

The above description has focused on providing the disclosed locomotion system in an endoscopic capsule. However, this is merely an example and the locomotion system can be provided in any suitable medical device. Other example suitable devices include radio-opaque pellets used for diagnosis.

The locomotion system can be used in medical devices for use in both humans and non-human animals.

The locomotion system disclosed can be used throughout the device's passage through the body or can be switched on at opportune moments when needed. That is, the locomotion provided can be used instead of or in addition to the natural passage of the device through the body.

The medical device can be configured to comprise other components as well as the locomotion device, for example an imaging means or a vibration mechanism.

While various specific combinations of components and method steps have been described, these are merely examples. Components and method steps can be combined in any suitable arrangement or combination. Components and method steps can also be omitted to leave any suitable combination of components or method steps. In particular, except for those elements which must be necessarily different to achieve the desired functionality, the features of the first and second embodiments described above can be combined freely. Where corresponding principles apply, descriptions of benefits and functionality described with respect to the first embodiment apply to the second embodiment and vice versa.

Throughout the discussion of the disclosed embodiments, various relative direction terms such as "left" and "right" have been used. These are to be understood as entirely non-limiting and are provided merely to aid understanding. It will be appreciated that the disclosed device can be used in any orientation, and component parts can move in any suitable direction relative to one another.

The singular terms "a" and "an" should not be taken to mean "one and only one". Rather, they should be taken to mean "at least one" or "one or more" unless stated otherwise. The word "comprising" and its derivatives including "comprises" and "comprise" include each of the stated features, but does not exclude the inclusion of one or more further features.

The above implementations have been described by way of example only, and the described implementations are to be considered in all respects only as illustrative and not restrictive. It will be appreciated that variations of the described implementations can be made without departing from the scope of the disclosure. It will also be apparent that there are many variations that have not been described, but that fall within the scope of the appended claims.

Additional aspects and features of the present disclosure are set forth in the following numbered clauses.

The invention claimed is:

1. A locomotion system for use in a medical device, comprising:
an actuator comprising a plurality of coil windings;
a ferromagnetic member; and
a plurality of magnets, wherein the plurality of magnets are arranged circumferentially around the actuator and ferromagnetic member;

14 wherein the actuator is configured, on application of a current to the plurality of coil windings, to travel along the ferromagnetic member and to impact on a surface.

2. The locomotion system of claim 1, further comprising a housing.

3. The locomotion system of claim 2, wherein the surface is a surface of the housing.

4. The locomotion system of claim 2, wherein the ferromagnetic member is located centrally within the housing.

5. The locomotion system of claim 2, wherein the actuator is not in sliding contact with the housing as it travels along the ferromagnetic member.

6. The locomotion system of claim 1, wherein the ferromagnetic member comprises a rod or rail, and wherein the actuator is configured to slide along the rod or rail.

7. The locomotion system of claim 1, wherein the actuator comprises a carriage around which is wound the plurality of coil windings.

8. The locomotion system of claim 1, further comprising a returning element configured to repel the actuator from the surface.

9. The locomotion system of claim 8, wherein the returning element comprises a spring or an additional magnet.

10. The locomotion system of claim 1, wherein the locomotion system is an endoscopic capsule.

11. A method of moving a medical device with a locomotion system comprising an actuator comprising a plurality of coil windings, a ferromagnetic member, and a plurality of magnets, wherein the plurality of magnets are arranged circumferentially around the actuator and ferromagnetic member, wherein the actuator is configured, on application of a current to the plurality of coil windings, to travel along the ferromagnetic member and to impact on a surface, the method comprising:
applying a first current to the plurality of coil windings to cause the actuator to travel along the ferromagnetic member in a first direction and impact on the surface, wherein the actuator impacting on the surface generates motion of the medical device in the first direction.

12. The method of claim 11, further comprising moving the actuator in a second direction away from the surface.

13. The method of claim 12, wherein moving the actuator in the second direction comprises applying a second current to the plurality of coil windings, said second current having an opposite polarity to the first current such that application of the second current causes the actuator to travel along the ferromagnetic member in the second direction.

14. The method of claim 11, wherein an endoscopic capsule comprises the locomotion system.

15. A method for the diagnosis of a disease or condition in a subject using a medical device comprising a locomotion system including an actuator comprising a plurality of coil windings, a ferromagnetic member, and a plurality of magnets, wherein the plurality of magnets are arranged circumferentially around the actuator and ferromagnetic member; wherein the actuator is configured, on application of a current to the plurality of coil windings, to travel along the ferromagnetic member and to impact on a surface, the method comprising:
generating images of the gastrointestinal tract of said subject using an imaging means located in the medical device when said medical device is located in the gastrointestinal tract; and
analyzing said images to determine a presence or absence of the disease or condition.

16. The method of claim 15, wherein an endoscopic capsule comprises the locomotion system.

17. An endoscopic capsule comprising:

a locomotion system including:

an actuator comprising a plurality of coil windings, a ferromagnetic member, and a plurality of magnets, wherein the plurality of magnets are arranged circumferentially around the actuator and ferromagnetic member, and wherein the actuator is configured, on application of a current to the plurality of coil windings, to travel along the ferromagnetic member and to impact on a surface.

* * * * *